(12) United States Patent
Bandhauer et al.

(10) Patent No.: US 6,767,363 B1
(45) Date of Patent: Jul. 27, 2004

(54) ACCOMMODATING POSITIVE AND NEGATIVE INTRAOCULAR LENS SYSTEM

(75) Inventors: Mark H. Bandhauer, Orange, CA (US); George F. Green, St. Louis, MO (US); Donald Carrol Stenger, Anaheim Hills, CA (US); Michael T. Landreville, New Port Coast, CA (US)

(73) Assignee: Bausch & Lomb Surgical, Inc., Rochester, NY (US)

( * ) Notice: Subject to any disclaimer, the term of this patent is extended or adjusted under 35 U.S.C. 154(b) by 0 days.

(21) Appl. No.: 09/434,635

(22) Filed: Nov. 5, 1999

(51) Int. Cl.[7] ................................................. A61F 2/16
(52) U.S. Cl. ...................................... 623/6.34; 623/6.37
(58) Field of Search ............................... 623/6.17, 6.22, 623/6.32, 6.34, 6.37, 6.38, 6.43, 6.44, 6.49, 6.51, 6.11, FOR 105, 6.13

(56) References Cited

U.S. PATENT DOCUMENTS

| | | | |
|---|---|---|---|
| 4,892,543 A | | 1/1990 | Turley |
| 5,047,051 A | | 9/1991 | Cumming |
| 5,275,623 A | | 1/1994 | Sarfarazi |
| 5,326,347 A | | 7/1994 | Cumming |
| 5,326,506 A | | 7/1994 | Vanderbilt |
| 5,391,202 A | | 2/1995 | Lipshitz |
| 5,476,514 A | | 12/1995 | Cumming |
| 5,496,366 A | | 3/1996 | Cumming |
| 5,674,282 A | | 10/1997 | Cumming |
| 5,928,282 A | | 7/1999 | Nigam |
| 6,096,078 A | * | 8/2000 | McDonald ............. 623/6.37 X |
| 6,488,708 B2 | * | 12/2002 | Sarfarazi .................... 623/6.34 |
| 2003/0060881 A1 | * | 3/2003 | Glick et al. ................ 623/6.37 |

FOREIGN PATENT DOCUMENTS

| | | | | |
|---|---|---|---|---|
| DE | 195 01 444 A1 | * | 7/1996 | ............. A61F/2/16 |
| EP | 0 337 390 A | | 10/1989 | |
| JP | 2-126847 A | * | 5/1990 | ............. A61F/2/16 |
| WO | WO 89 06520 A | | 7/1989 | |
| WO | WO 99 20206 A | | 4/1999 | |
| WO | WO 00 66037 | | 11/2000 | |

OTHER PUBLICATIONS

Article: Accomodative Intraocular Lens with Spring Action Part 1. Design and Placement in an Excised Animal Eye Authors: Tsutomu Hara, M.D., Takako Hara, M.D., Akhiro Yasuda, and Yoshiharu Yamada pp.: 6 Date: Feb. 1990, Ophthalmic Surgery, vol. 21, No. 2, pp. 128–133.

Articles: Accomodative Intraocular Lens with Spring Action Part 2. Fixation in the Living Rabbit Aurthors: Tsutomu Hara, M.D., TakaoHara, M.D., Akihiro Yasuda, Eng., Yuriko Mizumoto, Eng. and Yasuharu Yamada, Eng. pp.: 4 Date: Sep. 1992, Ophthalmic Surgery, vol. 23, No. 9, pp. 632–635.

* cited by examiner

*Primary Examiner*—David H. Willse
(74) *Attorney, Agent, or Firm*—Katherine McGuire; Rita D. Vacca (57) ABSTRACT

An accommodating intraocular lens system including a higher diopter positive intraocular lens and a lower diopter negative intraocular lens. The positive intraocular lens includes a positive optic portion having an outer peripheral edge and two or more haptic elements. The negative intraocular lens includes a negative optic portion having an outer peripheral edge and two or more haptic elements. Each haptic element is formed to have specific flexibility characteristics so as to be less resistant to bending in a plane generally parallel to an eye's optical axis than in a plane generally perpendicular to the eye's optical axis. The accommodating intraocular lens system is so designed with specific flexibility characteristics to facilitate axial displacement of the positive optic portion with respect to the negative optic portion along the eye's optical axis under a compression force. Through the axial displacement of the positive optic portion with respect to the negative optic portion, accommodative effects are maximized to achieve multi-distance visual imaging.

21 Claims, 7 Drawing Sheets figure 1 figure 3 figure 4 figure 5 figure 6 figure 7 figure 8 figure 9 figure 10 figure 11 figure 12

ACCOMMODATING POSITIVE AND NEGATIVE INTRAOCULAR LENS SYSTEM

FIELD OF THE INVENTION

The present invention relates to an intraocular lens (IOL) system and a method for making and using the same. More particularly, the present invention relates to an accommodating IOL system designed for multi-distance visual imaging in aphakic eyes where a diseased natural lens has been surgically removed, such as in the case of cataracts.

BACKGROUND OF THE INVENTION

IOL implants have been used for many years in aphakic eyes as replacements for diseased natural crystalline lenses that have been surgically removed from the eyes. Many different IOL designs have been developed over past years and proven successful for use in aphakic eyes. Successful IOL designs to date primarily include an optic portion with supports therefor, called haptics, connected to and surrounding at least part of the optic portion. The haptic portions of an IOL are designed to support the optic portion of the IOL in the lens capsule, anterior chamber or posterior chamber of an eye.

Commercially successful IOLs have been made from a variety of biocompatible materials, ranging from more rigid materials such as polymethylmethacrylate (PMMA) to softer, more flexible materials capable of being folded or compressed such as silicones, certain acrylics, and hydrogels. Haptic-portions of the IOLs have been formed separately from the optic portion and later connected thereto through processes such as heat, physical staking and/or chemical bonding. Haptics have also been formed as an integral part of the optic portion in what is commonly referred to as "single-piece" IOLs.

Softer, more flexible IOLs have gained in popularity in more recent years due to their ability to be compressed, folded, rolled or otherwise deformed. Such softer IOLs may be deformed prior to insertion thereof through an incision in the cornea of an eye. Following insertion of the IOL in an eye, the IOL returns to its original pre-deformed shape due to the memory characteristics of the soft material. Softer, more flexible IOLs as just described may be implanted into an eye through an incision that is much smaller, i.e., 2.8 to 3.2 mm, than that necessary for more rigid IOLs, i.e., 4.8 to 6.0 mm. A larger incision is necessary for more rigid IOLs because the lens must be inserted through an incision in the cornea slightly larger than the diameter of the inflexible IOL optic portion. Accordingly, more rigid IOLs have become less popular in the market since larger incisions have been found to be associated with an increased incidence of postoperative complications, such as induced astigmatism.

After IOL implantation, both softer and more rigid IOLs are subject to compressive forces exerted on the outer edges thereof from natural brain-induced contraction and relaxation of the ciliary muscle and increases and decreases in vitreous pressure. Compressive forces of this kind are useful in a phakic eye for focusing the eye at various distances. Most commercially successful IOL designs for use in aphakic eyes have single focus optic portions that are fixed and focus the eye at only a certain fixed distance. Such fixed single focus IOLs require the wearing of glasses to change the focus of the eye. A few fixed bifocal IOLs have been introduced to the commercial market but suffer from the disadvantage that each bifocal image represents only about forty percent of the available light thus lessening visual acuity.

Because of the noted shortcomings of current IOL designs, there is a need for accommodating IOLs designed to provide improved visual imaging at various distances in aphakic eyes without the aid of eyeglasses.

SUMMARY OF THE INVENTION

An accommodating intraocular lens (IOL) system made in accordance with the present invention has a positive intraocular lens used in conjunction with a negative intraocular lens. The positive intraocular lens has a "higher" diopter, preferably approximately +20 diopter or greater, such as but not limited to +20 to +60 diopter, positive optic portion with an outer peripheral edge and two or more but preferably two, three or four haptic elements for supporting the optic portion in a patient's eye. The negative intraocular lens has a "lower" diopter, preferably approximately −10 diopter or less, such as but not limited to −10 to −50 diopter, negative optic portion also having an outer peripheral edge and preferably the same, but optionally a different number of haptics from that of the positive optic portion. Positive and negative intraocular lenses each having two haptic elements are balanced for stability within an eye to minimize decentration by having a haptic element integrally formed with or subsequently attached to two opposed edges of each of the two optic portions. Positive and negative intraocular lenses each having three haptic elements are balanced to achieve stability and minimize decentration by having a set of two haptic elements integrally formed with or subsequently attached to one edge of each of the optic portions and a third haptic element integrally formed with or subsequently attached to an opposite edge of each of the optic portions. Positive and negative lenses each having four haptic elements are balanced to achieve stability and minimize decentration by each optic portion having a set of two haptic elements integrally formed with or subsequently attached to one edge of the optic and a set of two haptic elements integrally formed with or subsequently attached to an opposite edge of the optic. Each haptic element has an attachment portion that permanently connects the haptic element to the outer peripheral edge of an optic portion. If the haptic element is of a looped design, the haptic element has generally two attachment portions that permanently connect the looped haptic element to the outer peripheral edge of the optic portion. In the case of lenses having three or four looped haptic elements, a set of two looped haptic elements may have three attachment portions rather than four. In such a case, one of the three attachment portions is common to each of the two looped haptic elements in the set. Each haptic element whether of a loop design or not includes a flexible central portion located between the attachment portion and a contact plate. The contact plate is designed to engage an inner surface of a patient's eye. The flexible central portions that extend between the contact plates and the attachment portions allow the optic portions of both the positive and negative lenses to move or to adjust to pressures exerted on the positive and negative lenses within the eye. Additionally, within these flexible central portions, each haptic element is designed to have less resistance to bending in a plane generally parallel to the optical axis of an eye than in a plane generally perpendicular to the optical axis of an eye. By providing haptic elements with this type of flexibility characteristic, the present accommodating IOL system achieves axial displacement of the positive optic portion with regard to the negative optic portion along the optical axis of the eye when compressive forces are exerted against the accommodating IOL system. Also, by combining a higher diopter positive optic portion with that of a lower diopter negative optic portion, an additive effect is achieved whereby even slight movement or axial displacement of the higher diopter positive optic portion with regard to the lower diopter negative optic portion achieves a significantly large increase in accommodative effect and improved multi-distance visual imaging without the aid of eyeglasses.

Accordingly, it is an object of the present invention to provide accommodating intraocular lens systems for use in aphakic eyes.

Another object of the present invention is to provide accommodating intraocular lens systems for use in aphakic eyes, which achieves axial displacement of the higher diopter optic portion with regard to the lower diopter optic portion along the optical axis of the eyes.

Another object of the present invention is to maximize accommodative effects of the intraocular lens system with even minimal optic axial displacement.

Another object of the present invention is to provide accommodating intraocular lens systems for use in aphakic eyes, which minimize damage to tissues in the interior of the eyes.

Still another object of the present invention is to provide accommodating intraocular lens systems, which are resistant to decentration within the eyes.

These and other objectives and advantages of the present invention, some of which are specifically described and others that are not, will become apparent from the detailed description, drawings and claims that follow, wherein like features are designated by like numerals.

DETAILED DESCRIPTION OF THE INVENTION

Figure 1:
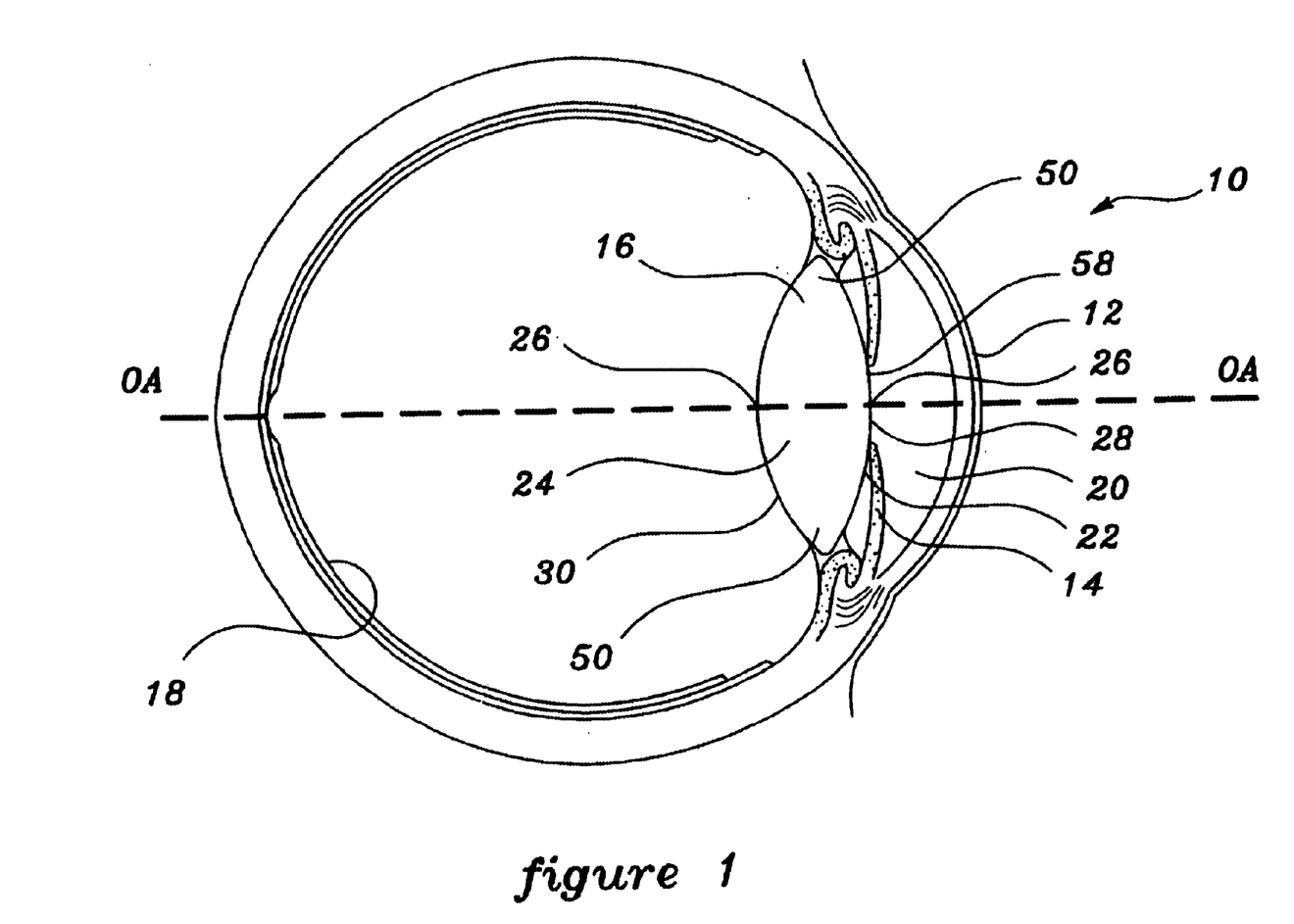
FIG. 1 is a schematic representation of the interior of a human eye.

FIG. 1 illustrates a simplified diagram of an eye 10 showing landmark structures relevant to the implantation of an intraocular lens of the present invention. Eye 10 includes an optically clear cornea 12 and an iris 14. A natural crystalline lens 16 and a retina 18 are located behind the iris 14 of eye 10. Eye 10 also includes anterior chamber 20 located in front of iris 14 and a posterior chamber 22 located between iris 14 and natural lens 16. Accommodating IOL systems of the present invention are preferably implanted in lens capsule 24 after the removal of diseased natural lens 16. Eye 10 also includes an optical axis OA—OA that is an imaginary line that passes through the optical center 26 of anterior surface 28 and posterior surface 30 of natural lens 16. Optical axis OA—OA in the human eye 10 is generally perpendicular to a portion of cornea 12, natural lens 16 and retina 18.

Figure 2:
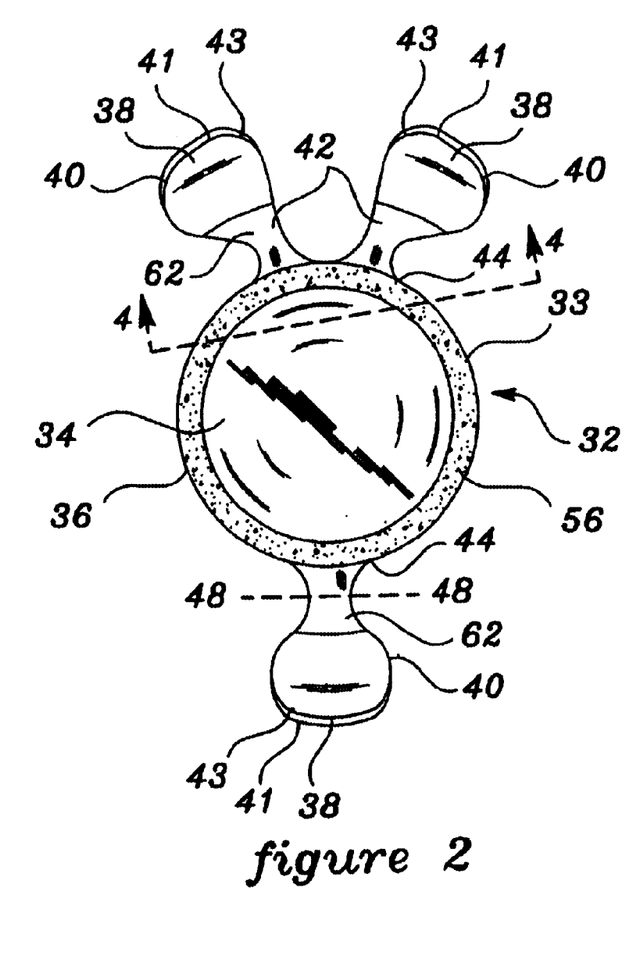
FIG. 2 is a plan view of an accommodating IOL system with each optic portion having three haptics made in accordance with the present invention.
Figure 3:
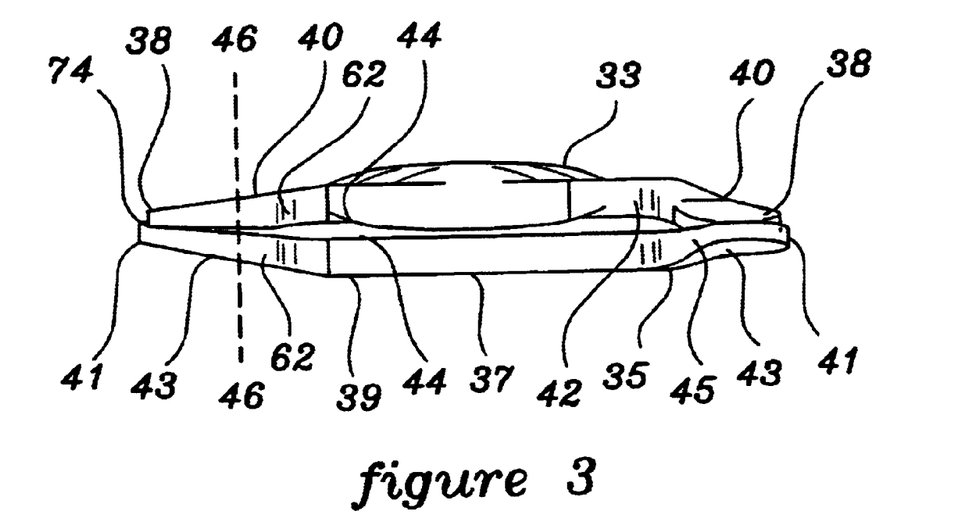
FIG. 3 is a side view of the IOL system of FIG. 2.
Figure 4:
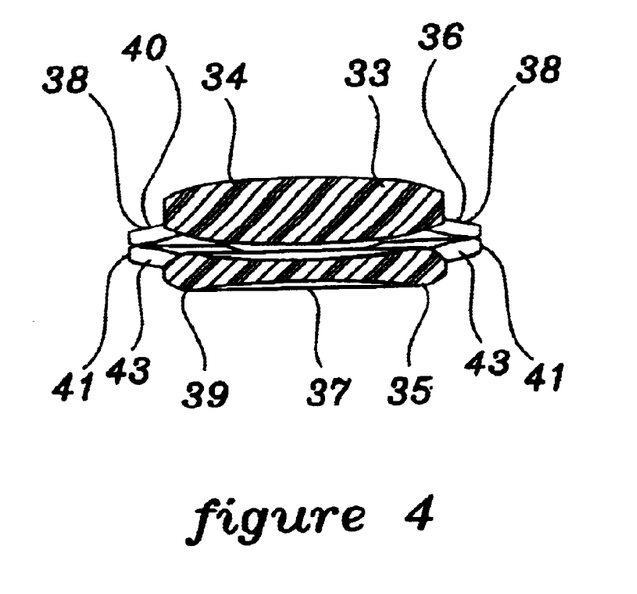
FIG. 4 is a cross sectional view of the IOL system of FIG. 2 taken along line 4—4.
Figure 5:
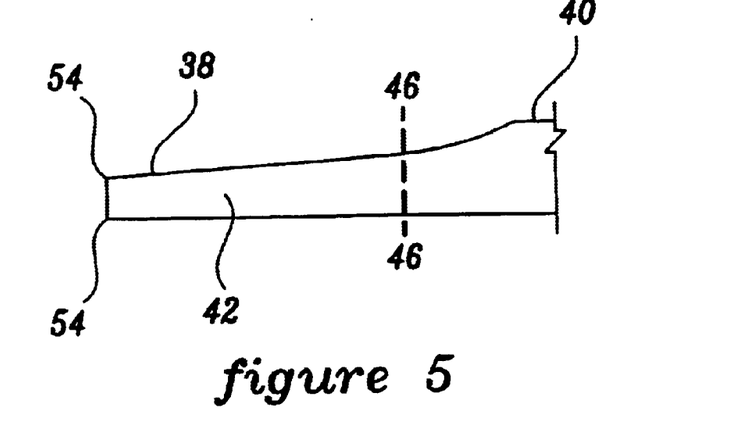
FIG. 5 is a side view of the haptic elements of FIG. 3 with sharper edges.
Figure 6:
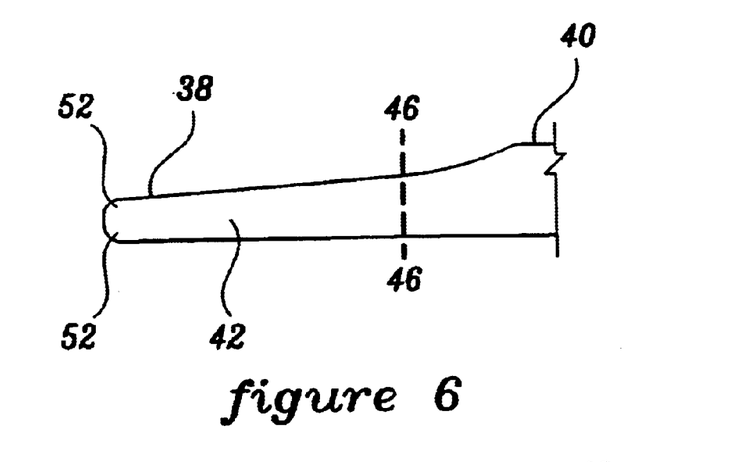
FIG. 6 is a side view of the haptic elements of FIG. 3 with rounded edges.
Figure 7:
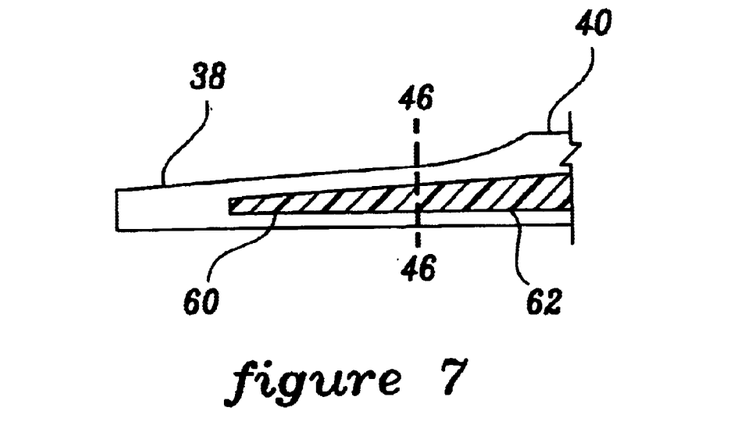
FIG. 7 is a cross sectional view of the haptic elements of FIG. 5 with a stiffening element.
Figure 8:
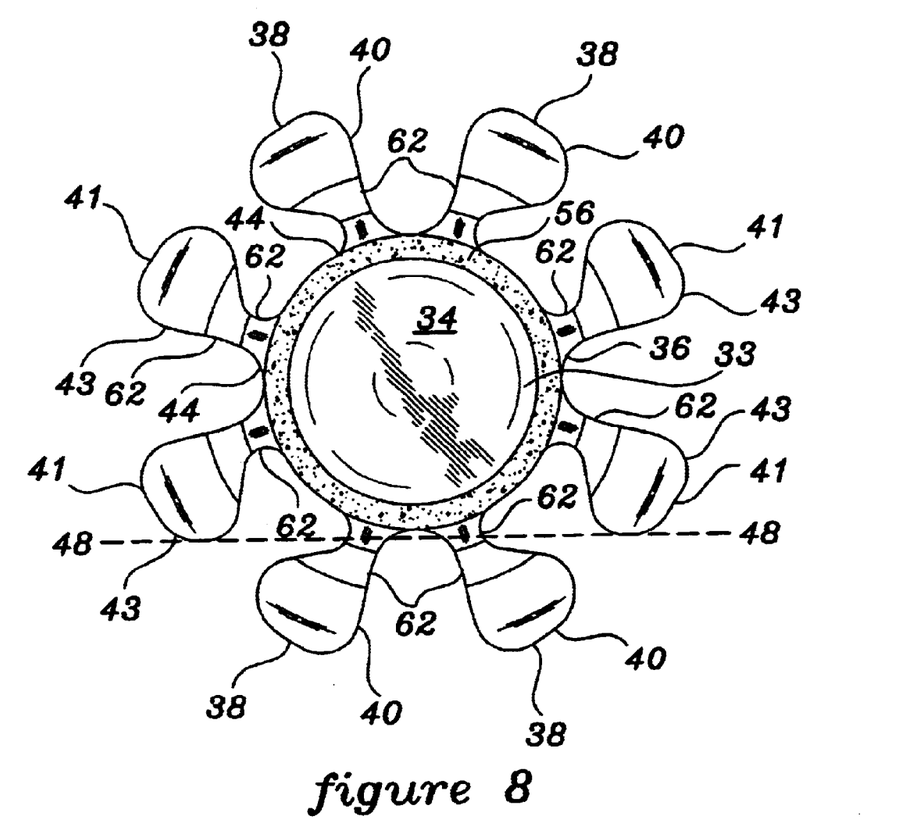
FIG. 8 is a plan view of an accommodating IOL system with each optic portion having four haptics made in accordance with the present invention.
Figure 9:
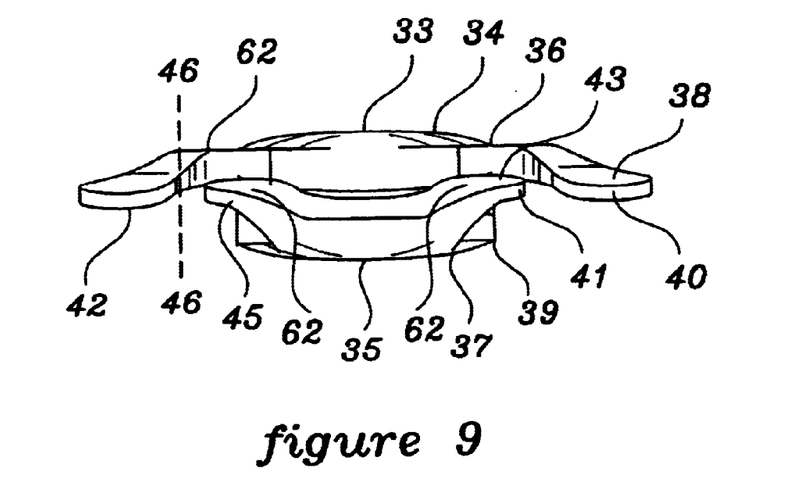
FIG. 9 is a side view of the IOL system of FIG. 8.
Figure 10:
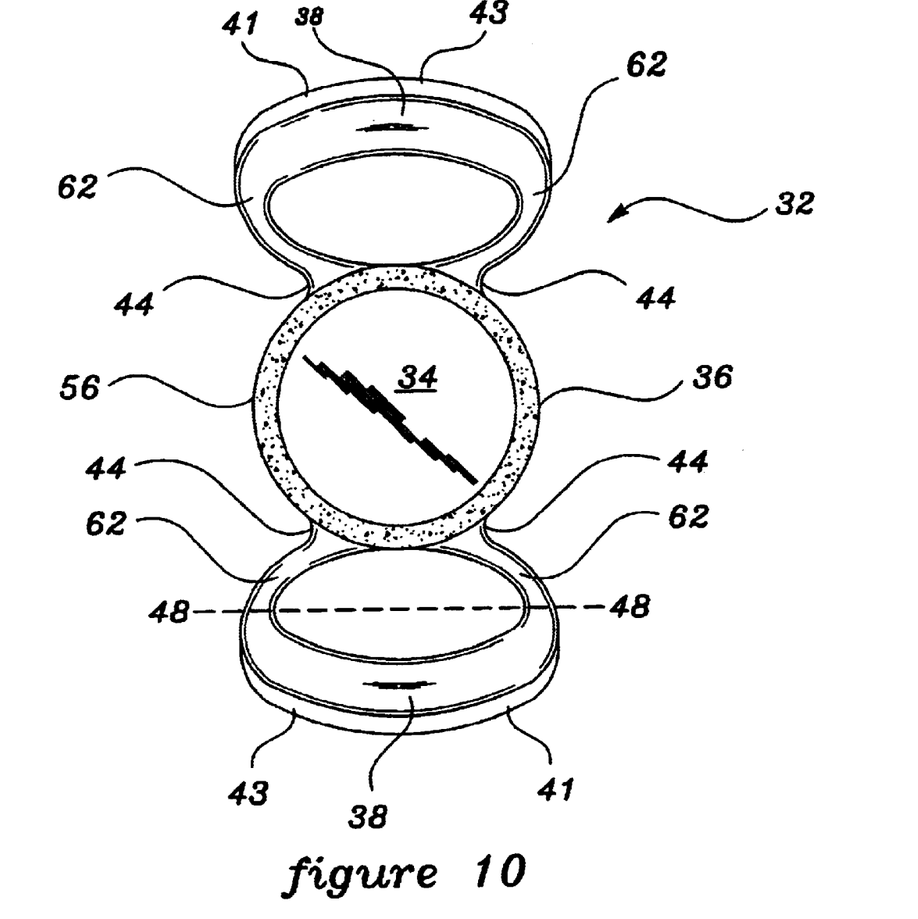
FIG. 10 is a plan view of an accommodating IOL system with each optic portion having two haptics made in accordance with the present invention.
Figure 11:
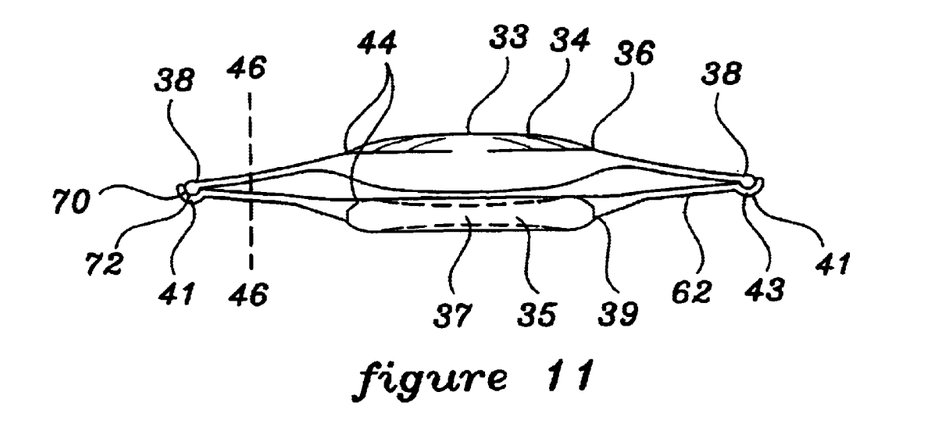
FIG. 11 is a side view of the IOL of FIG. 10.
Figure 12:
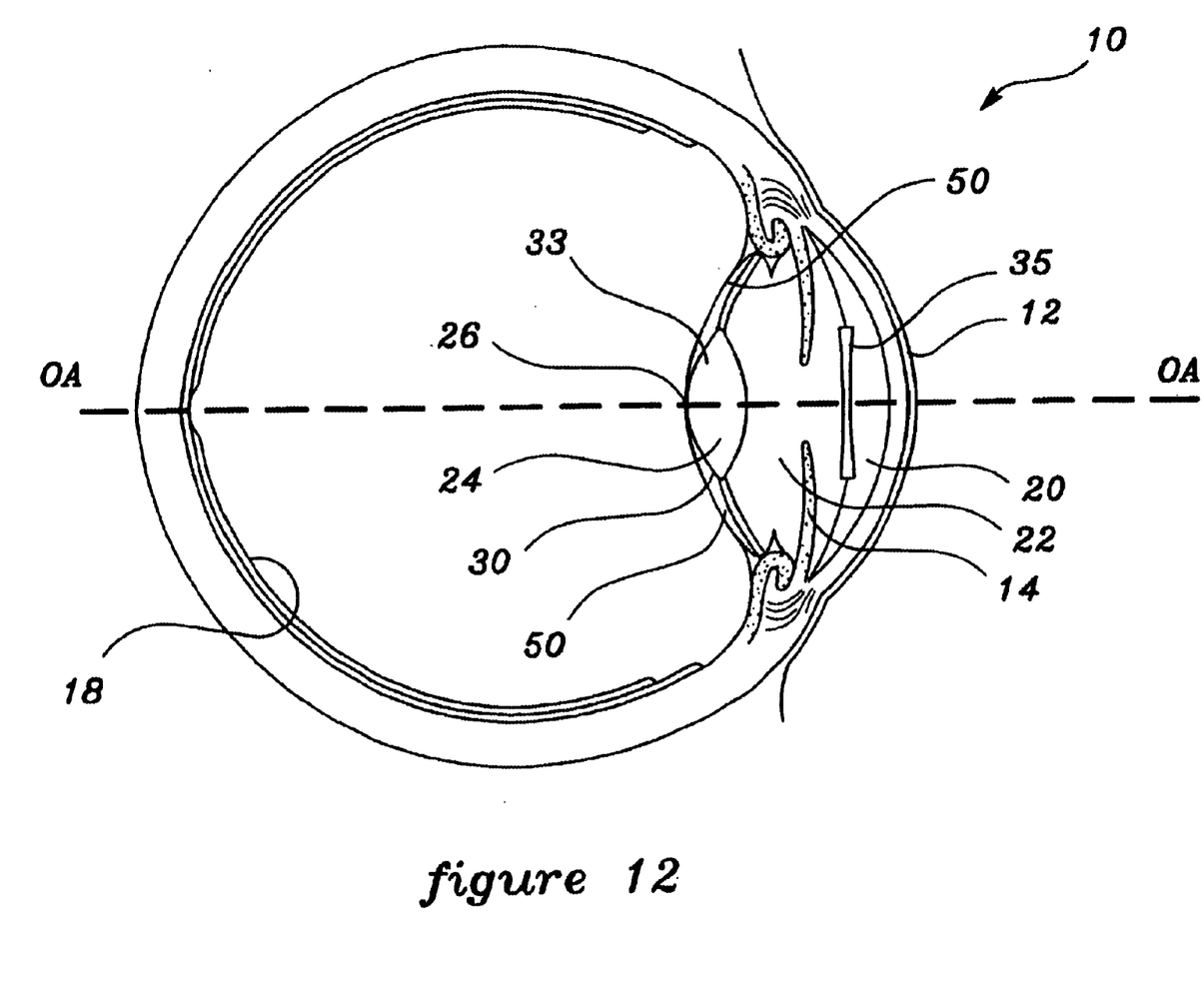
FIG. 12 is the view of FIG. 1 and further showing an embodiment of the invention where the positive lens is implanted in the capsule and the negative lens is implanted in the eve's anterior chamber.

The IOL system of the present invention, as illustrated in FIGS. 2 through 11 but best illustrated in FIGS. 2, 8 and 10, is identified generally by reference numeral 32. IOL system 32 comprises a positive lens 33 having a higher diopter optic portion 34 with an outer peripheral edge 36 and a negative lens 35 having a lower diopter optic portion 37 with an outer peripheral edge 39. IOL system 32 is designed for implantation preferably in lens capsule 24 of a patient's eye 10. Alternatively, positive lens 33 may be placed in lens capsule 24 and negative lens 35 may be manufactured as a standard anterior chamber intraocular lens to minimize tissue damage, such as that disclosed in U.S. Pat. No. 5,300,117, incorporated herein in its entirety by reference, and positioned within anterior chamber 20. When IOL system 32 is positioned within lens capsule 24 of eye 10, positive lens 33 is preferably positioned anterior to negative lens 35 and anteriorly vaulted, i.e., vaulted toward iris 14, and negative lens 35 positioned posterior to positive lens 33 and posteriorly vaulted, i.e., vaulted toward retina 18. A vault of approximately 1.0 to 2.0 mm measuring from the plane of outer peripheral edges 36 and 39 of optic portions 34 and 37 respectively to the plane of haptic contact plates 38 and 41 respectively, described in detail below, is generally suitable. Preferably integrally formed on peripheral edges 36 and 39 of optic portions 34 and 37 are two or more but preferably two, three or four looped or non-looped haptic elements 40 and 43 respectively, each having an edge portion 42 and 45 respectively. Haptic elements 40 and 43 are preferably integrally formed with and permanently connected to outer peripheral edges 36 and 39 of optic portions 34 and 37 by attachment portions 44. Alternatively however, haptic elements 40 and 43 may be attached to optic portions 34 and 37 by staking, chemical polymerization or other methods known to those skilled in the art. Each haptic element 40 and 43 also includes a broadened contact plate 38 and 41 respectively designed to preferably engage inner surfaces 50 in lens capsule 24 of eye 10. Broadened contact plates 38 and 41 may be designed for direct contact as illustrated in FIGS. 3 and 11. Such designs may include, but are not limited to, contact plate 41 having a trough 70 and contact plate 38 having a ridge 72 to achieve preferably nonpermanent, but alternatively permanent, interlocking of positive lens 33 and negative lens 35 (FIG. 11) or an extended tab 74 on edge 45 of contact plate 41 to achieve preferably nonpermanent, but alternatively permanent, interlocking with edge 42 of contact plate 38 of positive lens 33 (FIG. 3). As another alternative, best illustrated in FIG. 8, contact plates 38 and 41 of positive lens 33 and negative lens 35 may be positioned so as to avoid direct contact upon placement within lens capsule 24.

In accordance with the present invention, haptic elements 40 and 43 are designed so that when IOL system 32 is implanted in the lens capsule 24 of a patient's eye 10 and held in place through compressive forces exerted by inner surfaces 50 on contact plates 38 and 41 of haptic elements 40 and 43 respectively, haptic elements 40 and 43 flex so that contact plates 38 and 41 do not slide along surfaces 50 in eye 10. Accordingly, haptic elements 40 and 43 are designed to flex in a plane generally perpendicular to that of optic portions 34 and 37 of IOL system 32 and generally parallel to that of optical axis OA—OA of eye 10. Haptic elements 40 and 43 flex to achieve displacement of lens 33 with respect to lens 35. When IOL system 32 is implanted within lens capsule 24, lens 35 may be fixed whereby only lens 33 is axially displaced to achieve multi-distance visual imaging. However, it is preferable to maximize accommodative effects through opposed axial displacement of both lenses 33 and 35. By using a higher diopter lens 33 and designing this type of flexibility characteristic into haptic elements 40 and 43, IOL system 32 achieves maximum accommodative effect to allow an eye to achieve multi-distance visual imaging without the aid of eyeglasses. The flexibility characteristic and vaulting of haptic elements 40 and 43 enables axial displacement of optic portions 34 and 37 in opposite directions along optical axis OA—OA of eye 10. Compressive forces of differing magnitudes within the range of approximately 0.1 to 5 mN exerted against contact plates 38 and 41 of haptic elements 40 and 43 to effect approximately an overall 1.0 mm in diameter compression of IOL system 32, such as that caused by natural brain-induced forces within eye 10, results in approximately 1.0 mm to 3.0 mm combined opposed axial displacement of optic portions 34 and 37 along optical axis OA—OA in an eye 10. By combining a higher diopter positive optic portion with that of a lower diopter negative optic portion, an additive effect is achieved whereby even slight movement or axial displacement of the higher diopter positive optic portion with regard to the lower diopter negative optic portion results in a disproportionately large increase in accommodative effect and improved multi-distance visual imaging without the aid of eyeglasses. For example, if one were to use a +50 diopter positive intraocular lens in conjunction with a −30 diopter negative intraocular lens for a combined +20 diopter effect, one achieves at least double the accommodative effect achieved using a single +20 diopter positive intraocular lens. By adding axial displacement of the higher diopter positive lens with respect to the lower diopter negative lens, the accommodative effects of the IOL system 32 are even greater. The IOL system 32 of the present invention with its maximized accommodative effects through the axial displacement of optic portion 34 with respect to optic portion 37 enables an eye to achieve multi-distance visual imaging when compressive forces are applied to eye 10 without the use of eyeglasses.

The flexibility characteristic of haptic elements 40 and 43 of IOL system 32 as described above is achieved through the unique design thereof. As best illustrated in FIG. 2, IOL system 32 has haptic elements 40 and 43 formed with flexible central portions 62 adjacent to attachment portions 44 permanently connected to outer peripheral edges 36 and 39 of optic portions 34 and 37 respectively. Flexible central portions 62 are essential in imparting the necessary flexibility to the IOLs of the present invention. Flexible central portions 62 have a dimension in plane 46—46 generally parallel to optical axis OA—OA, as depicted in FIGS. 3, 9 and 11, less than or equal to but most preferably less than the same in plane 48—48 generally perpendicular to optical axis OA—OA as depicted in FIGS. 2, 8 and 10. Contact plates 38 and 41 are relatively flat with either rounded edges 52 as depicted in FIG. 6 to provide a smoother fit with inner surfaces 50, or more defined, sharper edges 54 as depicted in FIG. 7 to provide a barrier to prevent cellular migration and growth upon implantation in lens capsule 24.

The subject IOL system 32 is preferably manufactured to have optic portions 34 and 37 approximately 4.5 to 9.0 mm, but preferably approximately 5.0 to 6.0 mm and most preferably approximately 5.5 to 6.0 mm in diameter and approximately 0.15 mm to 1.0 mm, but preferably approximately 0.6 to 0.8 mm and most preferably approximately 0.7 mm in thickness at peripheral edge 36. Haptic elements 40 and 43 extend from the optic portions 34 and 37 respectively of IOL system 32 in a generally rounded or oval configuration and will increase or decrease in overall length depending upon the size of IOL system 32 desired and the diameter of optic portions 34 and 37. As the diameter of optic portions 34 and/or 37 increases, the overall length of haptic elements 40 and/or 43 may be decreased. Likewise, as the diameter of optic portions 34 and/or 37 decreases, the overall length of haptic elements 40 and/or 43 may be increased. However, as customary, the overall length of the haptic elements 40 and 43 are varied to achieve desired IOL system 32 sizes rather than varying the sizes of optic portions 34 and/or 37. In general, looped haptic elements 40 and 43 as illustrated in FIGS. 2, 8 and 10 are formed to be approximately 2.6 to 6.0 mm, but preferably approximately 3.4 to 5.0 mm and most preferably approximately 4.2 mm in length measuring from a point of equal distance between common attachment portions 44 on peripheral edges 36 and 39, to the center of contact plates 38 and 41 respectively. Looped haptic elements 40 and 43 preferably have a generally rounded or oval configuration as illustrated in FIGS. 10 and 11 to allow axial deflection under compressive forces. Non-looped haptic elements 40 and 43 as illustrated in FIGS. 8 and 9 are formed to be approximately 2.6 to 6.0 mm, but preferably approximately 3.4 to 5.0 mm and most preferably approximately 4.2 mm in length measuring from the middle of attachment portion 44 on peripheral edges 36 and 39, to the center of contact plates 38 and 41 respectively. Non-looped haptic elements 40 and 43 preferably have a generally rounded or oval configuration as illustrated in FIGS. 8 and 9 to provide a suitable stable fit within lens capsule 24 while allowing axial deflection under compressive forces. For purposes of the present invention, the generally rounded or oval shape of looped and non-looped haptic elements 40 and 43, i.e., the beam curve shape, relative to the width to thickness ratio, i.e., the aspect ratio, of haptic elements 40 and 43 as described herein is critical to achieve suitable function. Flexible central portion 62 of haptic elements 40 and 43 is approximately 0.5 to 2.5 mm, but preferably approximately 1.0 to 2.0 mm and most preferably approximately 1.6 mm in length; approximately 0.2 to 1.0 mm, but preferably approximately 0.3 to 0.7 mm and most preferably approximately 0.46 mm in width in plane 48—48 and approximately 0.2 to 0.7 mm, but preferably approximately 0.3 to 0.6 and most preferably approximately 0.43 mm in thickness in plane 46—46. Contact plates 38 and 41 are approximately 0.8 to 2.5 mm, but preferably approximately 1.0 to 2.2 mm and most preferably approximately 1.8 mm in length, approximately 0.05 to 0.5 mm, but preferably approximately 0.1 to 0.4 mm and most preferably approximately 0.3 mm in thickness and approximately 0.6 to 1.5 mm, but preferably approximately 0.8 to 1.2 mm and most preferably approximately 1.0 mm in width.

As provided through the dimensions of IOL system 32 above, looped and non-looped haptic elements 40 and 43 are relatively thick in plane 48—48 at contact plates 38 and 41 through to attachment portions 44 and optic portions 34 and 37, with flexible central portions 62 preferably exhibiting a thinner dimension in plane 46—46 than that of the width in plane 48—48. Looped haptic elements 40 and 43 of the subject IOL system 32 tend to resist deflection into closer proximity with outer peripheral edges 36 and 39 respectively when a compression force is exerted against contact plates 38 and 41 to maximize axial displacement along optical axis OA—OA. When accommodating IOL system 32 is used as a refractive lens, stable, reliable multi-distance visual imaging is provided.

The desired flexibility characteristic of haptic elements 40 and 43 of IOL system 32 may likewise be achieved or enhanced by incorporating a stiffening element 60, in the shape of a wide, very thin ribbon, in one or more haptic elements 40 and 43, as illustrated in FIG. 8. Stiffening element 60 may be positioned in haptic elements 40 and 43 so that wide or broad flat face 62 is oriented in a plane parallel to that of plane 48—48 so as to be thin axially in a plane parallel to that of plane 46—46. Stiffening element 60 functions in a manner similar to that of an I-beam in construction to maximize axial displacement along optical axis OA—OA when compressive force is applied to contact plates 38 and 41.

Stiffening element 60 is formed of a less flexible material than that of IOL system 32. Suitable materials for stiffening element 60 include but are not limited to polymethyl methacrylate, polyimides, polyolefins, high-density polyethylenes, polyesters, nylons, metals or any biocompatible material with suitable stiffening characteristics. Stiffening element 60 may be fabricated using one or more layers of a mesh, screen, webbing and/or sheet to impart the desired flexibility characteristics described herein. Stiffening element 60 may be used in conjunction with haptic elements 40 and 43 described above in cases where a thinner haptic design is desired while still achieving the desired stability and flexibility characteristics.

Suitable materials for the production of the subject IOL system 32 include but are not limited to foldable or compressible materials, such as silicone polymers, hydrocarbon and fluorocarbon polymers, hydrogels, soft acrylic polymers, polyesters, polyamides, polyurethane, silicone polymers with hydrophilic monomer units, fluorine-containing polysiloxane elastomers and combinations thereof. The preferred material for the production of IOL system 32 of the present invention is a hydrogel made from 2-hydroxyethyl methacrylate (HEMA) and 6-hydroxyhexyl methacrylate (HOHEXMA), i.e., poly(HEMA-co-HOHEXMA). Poly(HEMA-co-HOHEXMA) is the preferred material for the manufacture of IOL 32 due to its equilibrium water content of approximately 18 percent by weight, and high refractive index of approximately 1.474, which is greater than that of the aqueous humor of the eye, i.e., 1.336. A high refractive index is a desirable feature in the production of IOLs to impart high optical power with a minimum of optic thickness. By using a material with a high refractive index, visual acuity deficiencies may be corrected using a thinner IOL. Poly(HEMA-co-HOHEXMA) is a desirable material in the production of IOL system 32 due to its mechanical strength, which is suitable to withstand considerable physical manipulation. Poly(HEMA-co-HOHEXMA) also has desirable memory properties suitable for IOL use. IOLs manufactured from a material possessing good memory properties such as those of poly(HEMA-co-HOHEXMA) unfold in a more controlled manner in an eye, rather than explosively, to its predetermined shape. The unique design of the subject IOL system 32 with haptic elements 40 and 43 manufactured from a material having good memory properties also provides improved control of haptic unfolding upon insertion thereof in eye 10. Explosive unfolding of IOLs is undesirable due to potential damage to delicate tissues within the eye. Poly(HEMA-co-HOHEXMA) also has dimensional stability in the eye, which is desirable.

Although the teachings of the present invention are preferably applied to soft or foldable IOLs formed of a foldable or compressible material, the same may also be applied to harder, less flexible lenses formed of a relatively rigid material such as polymethylmethacrylate (PMMA) having flexible haptics formed either of the same or a different material.

Positive optic portion 34 of IOL system 32 can be a positive powered lens of approximately +20 diopter or greater but preferably approximately +20 to +60 diopter and negative optic portion 37 of IOL system 32 can be a negative powered lens of approximately −10 diopter or less but preferably −10 to −50 diopter. Optic portions 34 and 37 may be a combination of biconvex, plano-convex, plano-concave, biconcave, concave-convex (meniscus) or a diffractive-type lens element of any shape, depending upon the power required to achieve the appropriate accommodative effects for multi-distance visual imaging and to achieve appropriate central and peripheral thickness for efficient handling and fit within the eye 10. From the perspective of fit within eye 10 and performance, preferably positive lens 33 is convex-plano and negative lens 35 is plano-convex so the plano surface of positive lens 33 is in close proximity to the plano surface of negative lens 35, but most preferably, positive lens 33 is convex-plano and negative lens 35 is concave-plano so the plano surface of positive lens 33 is in close proximity to the concave surface of negative lens 35.

Optic portions 34 and 37 of the subject IOL system 32 may optionally be formed with a glare reduction zone 56 of approximately 0.25 to 2.00 mm but more preferably approximately 0.3 to 0.6 mm and most preferably 0.5 mm in width adjacent outer peripheral edge 36 and 39 for reducing glare when outer peripheral edge 36 and 39 of IOL system 32 is struck by light entering eye10 during high light or at other times when pupil 58 is dilated. Glare reduction zone 56 is typically fabricated of the same material as optic portions 34 and 37, but may be opaque, colored or patterned in a conventional manner to block or diffuse light in plane with optical axis OA—OA.

Subject IOL system 32 may or may not be of a unitary design and may be molded or most preferably manufactured by first producing disks from a material of choice as described in U.S. Pat. Nos. 5,217,491 and 5,326,506, each incorporated herein in its entirety by reference. If manufactured from disks, positive and negative lenses 33 and 35 respectively, are machined from material disks in a conventional manner. Once machined or molded, positive and negative lenses 33 and 35 may be polished, cleaned, sterilized and packaged by a conventional method known to those skilled in the art.

Subject IOL system 32 is used in eye 10 by creating an incision in cornea 12 and capsule 24, removing natural lens 16, inserting negative lens 35 and positive lens 33 as a unitary device or individually into capsule 24 and closing the incision. Preferably, lenses 35 and 33 are inserted into capsule 24 individually to allow for easier lens folding and smaller incision size. Alternatively, the subject IOL system 32 may be used in eye 10 by creating an incision in cornea 12 and capsule 24, removing natural lens 16, inserting positive lens 33 into capsule 24, inserting negative lens 35 into anterior chamber 20 and closing the incision.

IOL system 32 of the present invention provides for an accommodating lens suitable for use in an aphakic eye 10. IOL system 32 comprises two intraocular lens each having haptic elements 40 and 43 with flexibility characteristics that facilitate opposed axial displacement of optic portions 34 and 37 along optical axis OA—OA of eye 10 thereby enabling an eye to achieve multi-distance visual imaging without the aid of eyeglasses.

While there is shown and described herein certain specific embodiments of the present invention, it will be manifest to those skilled in the art that various modifications may be made without departing from the spirit and scope of the underlying inventive concept and that the same is not limited to the particular forms herein shown and described except insofar as indicated by the scope of the appended claims.

We claim:

1. An accommodating intraocular lens system to be implanted within an eye generally perpendicular to the eye's optical axis comprising:

a first outer peripheral edge defining a higher diopter positive optic portion with two or more haptic elements permanently connected to the first outer peripheral edge to form a positive lens, wherein said haptic elements each including a contact plate having a trough, and a second outer peripheral edge defining a lower diopter negative optic portion with two or more haptic elements permanently connected to the second outer peripheral edge to form a negative lens, said haptic elements each including a contact plate having a ridge interlockable with a respective said trough to interlock said positive and negative optic potions together, whereby said positive lens is adapted to move along the eye's optical axis relative to the negative lens to achieve an accommodative effect.

2. An accommodating intraocular lens system of claim 1 whereby a compressive force sufficient to effect a 1.0 mm in diameter compression of said lens system or said positive lens results in approximately 1.5 mm of axial displacement of said positive optic portion with respect to said negative optic portion along the eye's optical axis to enable an eye to achieve multi-distance visual imaging.

3. An accommodating intraocular lens system of claim 1 whereby a compressive force sufficient to effect a 1.0 mm in diameter compression of said lens system or said positive lens results in approximately 2.0 mm of axial displacement of said positive optic portion with respect to said negative optic portion along the eye's optical axis to enable an eye to achieve multi-distance visual imaging.

4. The intraocular lens system of claim 1 wherein said negative optic portion is fixed.

5. The intraocular lens system of claim 1 wherein said haptic elements and said optic portions are formed of a foldable or compressible material.

6. The intraocular lens system of claim 1 wherein said positive and negative optic portions are formed from the same or differing materials selected from the group consisting of silicone polymers, hydrocarbon and fluorocarbon polymers, hydrogels, soft acrylic polymers, polyester, polyamides, polyurethane, silicone polymers with hydrophilic monomer units, fluorine-containing polysiloxane elastomers and combinations thereof.

7. The intraocular lens system of claim 1 wherein either one or both of said positive and negative optic portions are formed from a hydrogel material.

8. The intraocular lens system of claim 1 wherein either one or both of said positive and negative optic portions are formed from a hydrogel material that is 18 percent by weight water.

9. The intraocular lens system of claim 1 wherein either one or both of said positive and negative optic portions are formed from poly(HEMA-co-HOHEXMA).

10. The intraocular lens system of claim 1 wherein either one or both of said positive and negative optic portions are formed from a material having a refractive index above 1.336.

11. The intraocular lens system of claim 1 wherein said lens system is formed from an acrylic material.

12. The intraocular lens system of claim 1 wherein said lens system is formed from a silicone material.

13. The intraocular lens system of claim 1 wherein said haptic elements are formed with a dimension in a plane generally perpendicular to the eye's optical axis to be greater than or equal to a dimension in a plane generally parallel to the eye's optical axis.

14. The intraocular lens system of claim 1 wherein a glare reduction zone is formed adjacent to the outer peripheral edge of either one or both of said positive and negative optic portions.

15. The intraocular lens system of claim 1 wherein one or more of said haptic elements includes a stiffening element having less resistance to bending in a plane generally parallel to an eye's optical axis than in a plane generally perpendicular to the eye's optical axis.

16. The intraocular lens system of claim 1 wherein one or more of said haptic elements includes a stiffening element formed from the same or differing materials selected from the group consisting of polymethyl methacrylate, polyimide, polyolefin, high-density polyester, nylon and metal.

17. A method of manufacturing the intraocular lens system of claim 1 comprising:

forming two disks from the same or different suitable materials, machining a positive lens from one disk, and machining a negative lens from the other disk.

18. A method of manufacturing the intraocular lens system of claim 1 comprising:

molding a positive lens of a suitable material, and molding a negative lens of a suitable material.

19. A method of using the intraocular lens system of claim 1 comprising:

creating an incision in a cornea and lens capsule of an eye, removing a natural lens of said eye, inserting a higher diopter positive intraocular lens into said lens capsule of said eye, and inserting a lower diopter negative intraocular lens into an anterior chamber of said eye.

20. An accommodating intraocular lens system of claim 1, whereby a compressive force sufficient to effect a 1.0 mm in diameter compression of said lens system or said positive lens results in approximately 1.0 mm of axial displacement of said positive optic portion with respect to said negative optic portion along the eye's optical axis to enable an eye to achieve multi-distance visual imaging.

21. An accommodating intraocular lens system to be implanted within an eye generally perpendicular to the eye's optical axis comprising:

a first outer peripheral edge defining a higher diopter positive optic portion with two or more haptic elements permanently connected to the first outer peripheral edge to form a positive lens, wherein said haptic elements each including a contact plate having a edge, and a second outer peripheral edge defining a lower diopter negative optic portion with two or more haptic elements permanently connected to the second outer peripheral edge to form a negative lens, said haptic elements each including a contact plate having a extended tab interlockable with a respective said edge to interlock said positive and negative optic portions together, whereby said positive lens is adapted to move along the eye's optical axis relative to the negative lens to achieve an accommodative effect.

* * * * *